United States Patent [19]

Godrej et al.

[11] Patent Number: 4,605,430

[45] Date of Patent: Aug. 12, 1986

[54] PLANT GROWTH PROMOTER FROM RICE BRAN AND PROCESSES FOR MAKING AND USING

[75] Inventors: Nadir B. Godrej; Manmohan S. Thakur, both of Bombay, India

[73] Assignee: Godrej Soaps Private Limited, Bombay, India

[21] Appl. No.: 670,175

[22] Filed: Nov. 9, 1984

[51] Int. Cl.4 ............................................. C05F 11/00
[52] U.S. Cl. ........................................... 71/23; 71/27; 71/64.08
[58] Field of Search ................ 71/23, 11, 27, 1, 64.10, 71/64.09, 64.08

[56] References Cited

FOREIGN PATENT DOCUMENTS 2105699  3/1983  United Kingdom .................... 71/23

OTHER PUBLICATIONS

"Science" article, vol. 195, dated Mar. 25th 1977, pp. 1339–1341.
"Science" article, vol. 212, dated Apr. 3, 1981, pp. 33–34.

Primary Examiner—Ferris H. Lander
Attorney, Agent, or Firm—Hill, Van Santen, Steadman & Simpson

[57] ABSTRACT

A plant growth promoter derived from rice bran fatty acid distillation residues is provided along with a process for the preparation thereof. A process for purification is provided. Also, compositions for using the plant growth promoter are described, together with processes for their preparation. Further, techniques for using the plant growth promoter are taught.

56 Claims, No Drawings

PLANT GROWTH PROMOTER FROM RICE BRAN AND PROCESSES FOR MAKING AND USING

BACKGROUND OF THE INVENTION

1. Field of the Invention

This invention relates to plant growth promoters, and especially to plant growth promoters derived from plant material.

2. Prior Art

Alfalfa (*Medicago sativa L.*) and Triacontanol isolated therefrom are reported to increase plant growth and yield (Science Vol. 195 dated 25th March 1977, pages 1339-1341). Triacontanol is reported to be a long chain fatty alcohol having 30 carbon atoms.

BRIEF SUMMARY OF THE INVENTION

This invention relates to a plant growth promoter from rice bran fatty acid distillation residues and to a process for the preparation thereof. The invention also relates to a method for the preparation of a composition containing such plant growth promoter and to the resulting composition. The invention further relates to a method for achieving plant growth promotion using the herein provided plant growth promoter and composition containing the same.

An object of the present invention is to provide a plant growth promoter from rice bran fatty acid distillation residue.

Another object of the invention is to provide a process for the isolation of said plant growth promoter.

Another object of the invention is to provide a process for the preparation of a composition containing said plant growth promoter.

Another object of the invention is to provide a composition containing said plant growth promoter which is useful in employing the said plant growth promoter for plant growth promotion. Another object of the invention is to provide a method for using said plant growth promoter and said composition for achieving plant growth promotion.

Other and further objects, aims, features, advantages, purposes, embodiments, applications, formulations, and the like within the spirit and scope of this invention will be apparent to those skilled in the art.

DETAILED DESCRIPTION

Rice bran oil, as those skilled in the art appreciate, is prepared from rice bran by a process of solvent extraction. Procedures for solvent extraction of rice bran are described in the literature for example "Industrial Oil and Fat Products" by Bailey.

The fatty acids of rice bran oil are separated therefrom usually by a process of distillation which normally consists of the following steps:

1. Crude rice bran oil is subjected to distillative deacidification to produce distilled fatty acids and neutral oil.
2. The neutral oil is hydrolysed to get crude fatty acids.
3. The crude fatty acids are distilled to produce distilled fatty acids and first residue.
4. The first residue is hydrolysed to get crude fatty acids.
5. The crude fatty acids are distilled to produce distilled fatty acids and final distillation residue.

Crude rice bran oil can also be hydrolysed directly without subjecting it to distillative deacidification.

Both the first and the final rice bran fatty acid distillation residues comprise unsaponifiables and other compounds, such as fatty acids and glycerides. A typical chemical analysis of the first rice bran fatty acid distillation residue is as follows:

| | |
|---|---|
| Unsaponifiables | 28.0% |
| Free fatty acids | 7.2% |
| Glycerides | 64.3% |
| Saponification value | 130.2 |

A typical chemical analysis of the final rice bran fatty acid distillation residue is as follows:

| | |
|---|---|
| Unsaponifiables | 44.5% |
| Free fatty acids | 6.8% |
| Glycerides | 48.7% |
| Saponification value | 88.7 |

The unsaponifiables comprise higher alcohols, wax, and sterols.

According to the present invention, there is provided a process for the preparation of a plant growth promoter from a starting rice bran fatty acid distillation residue. Such is derived from the distillation of crude fatty acids. Such crude fatty acid mixtures are themselves derived from crude rice bran oil by at least one process selected from the group consisting of (a) distillative deacidification, and
(b) hydrolysis.

Such processes are known to the art and are not part of the present invention.

Such starting residue is characterized by comprising on a 100 weight percent total residue basis:
from about 28 to 44.5 weight percent unsaponifiables,
from about 6.8 to 7.2 weight percent free fatty acids, and
from about 48.7 to 64.3 weight percent glycerides, and
said residue is further characterized by having a saponification value ranging from about 88.7 to 130.2.

In accord with this process, such a residue as so characterized is first saponified with alkali metal hydroxide. Thereafter, the resulting reaction mixture is treated with an alkaline earth metal salt (such a salt preferably contains an inorganic anion derived from a strong acid.) These steps are carried out under liquid phase conditions. As a result of the practice of these principal steps, the plant growth promoter in crude form is produced as a substantially water insoluble solid.

To separate such crude plant growth promoter from the associated liquid phase, the resulting reaction mixture is subjected to filtration (presently preferred) and/or centrifugation. Preferably, the resulting separated solids are dried before storage, use, or further treatment.

It is presently much preferred to purify and further isolate the plant growth promoter so obtained, particularly when such plant growth promoter is to be incorporated into a sprayable formulation for field application of growing crops to be treated therewith. A presently much preferred purification procedure involves the following steps:

(A) extracting the above-referenced separated solids (preferably dried, as described) with an organic solvent;

(B) concentrating the extracted solution:
(C) separating (e.g., filtering or centrifuging) solids from the concentrated extracted solution, and
(D) washing the so separated solids with an organic solvent.

The resulting so washed solids comprise purified plant growth promoter.

Either the first rice bran fatty acid distillation residue, or the final rice bran fatty acid distillation residue is preferably used for the saponification, but mixtures thereof may be employed. Such saponification may be carried out in an aqueous medium or in an organic solvent medium, or in a mixed liquid comprised of both water and organic liquid solvent. In the case of such a mixed liquid medium, it is preferably preferred to use water miscible organic solvents as the organic liquids.

The saponifying is preferably carried out by employing an initial weight ratio of said alkali metal hydroxide to said residue in the range from about 1:6 to 1:3 while maintaining a temperature ranging from about 80° to 100° C. for a time inversely extending from about 5 to 10 hours. Preferably, the liquid comprising such liquid phase itself comprises from about 100 to 200 weight percent of the total resulting saponified reaction mixture. Preferably, the saponifying is continued until a substantially complete saponification occurs.

Preferably, the alkali metal hydroxide used for saponification is selected from the group consisting of sodium hydroxide and potassium hydroxide. Preferably, the alkali metal hydroxide is preliminarily dissolved in water before being used for saponification. The saponification may be carried out, for example, in a 'Kadai' (vessel with hand paddle), in a soap kettle equipped with a mechanical stirrer, or the like.

When organic solvents are used for saponification, such may be, for example, a lower alkanol, such as ethanol or methanol. If the saponification is carried out under non-aqueous (organic) liquid conditions, then the organic solvent is removed by evaporation and the mass is dissolved in water. The resulting saponified reaction mixture contains alkali metal organic salts including alkali metal salts of fatty acids.

The total estimated quantity of alkali metal organic salts believed to be present in such a saponified reaction mixture which is prepared under the above indicated preferred conditions is believed to range characteristically from about 20 to 30 weight percent (based on total saponified reaction mixture).

The reaction mixture resulting from saponification of said residue with an alkali metal hydroxide is next treated with an alkaline earth metal salt to convert the alkali metal organic salts into alkaline earth metal salts. Conveniently, and preferably, such treatment is carried out by contacting such saponified reaction mixture with alkaline earth metal salt in an aqueous medium.

Preferably, the alkaline earth metal salt is preliminarily dissolved in water and preferably the alkaline earth metal salt is calcium chloride, barium chloride, and/or strontium chloride.

Preferably, such contacting is carried out by employing an initial weight ratio of said alkaline earth metal salt to total estimated said alkali metal organic salts in said resulting saponified reaction mixture in the range from about 1:2 to 1:1. Also, preferably, such contacting is carried out at a temperature ranging from about 25° to 50° C. for a time inversely extending from about 30 to 60 minutes.

The resulting reaction mixture contains precipitated solids which are separated by any convenient means from the associated liquid medium. Filtration or centrifugation can be used. A basket centrifuge is convenient, for example.

The recovered solids are preferably dried, as indicated. Air drying, for example, in an air oven at 130° to 140° C. for about 3 hours is suitable and convenient. Any convenient combination of drying times and mild temperatures may be employed.

In the above indicated purification procedure, the extraction of separated and preferably dried precipitate, is preferably a solvent done at a temperature in the range from about 40° C. to 55° C. While any convenient organic solvent maybe used for this extraction, presently preferred examples include acetone, isopropanol, and the like. The resulting extracted solution is conveniently concentrated, for example, by vaporizing or preferably distilling of a portion of the organic solvent to an extent which is at least sufficient to result in the appearance of a solid precipitate in the resulting residual solution.

The resulting concentrated extract system is then subjected to a separation (e.g., filtration or centrifugation). Filtration using paper or cloth is presently preferred.

The resulting separated and recovered solids are then washed with an organic solvent which is preferably acetone, isopropanol, or the like.

After washing, the resulting solids are preferably dried. Suitable drying conditions are as above indicated.

The plant growth promoter produced by the foregoing described process steps, including the purification procedure, is characterized by containing on a 100 weight percent total weight basis:
(A) from about 15 to 25 weight percent of triacontanol, with
(B) the balance up to 100 weight percent thereof being a mixture which is comprised of sterols, other fatty alcohols, wax, and impurities.

A presently preferred purified plant growth promoter contains about 20 weight percent triacontanol. The exact composition of the plant growth promoter is not now known, and the exact identity of the components in the plant growth promoter which promote plant growth is not now known, though it is theorized that more than one compound may be involved (but there is no intent herein to be bound by theory).

If desired, the plant growth promoter can be formulated. A preferred storage stable concentrate compositon of this invention for water dilution and subsequent treatment, such as by spraying of plants, will now be described. The water diluted composition prepared from such concentrate does not adversely affect absorption of minerals by plants. Such concentrate composition is conveniently prepared by the steps of:
(A) dissolving from about 0.2 to 2.0 parts by weight of nonionic surfactant in from about 99.5 to 95.6 parts by weight of water,
(B) dissolving from about 0.04 to 0.4 parts by weight of preservative in said water, and
(C) mixing from about 0.2 to 2.0 parts by weight of a purified (preferably as above described) plant growth promoter with said water while maintaining a temperature in the range from about 60° to 95° C., said mixing being carried out in the presence of said nonionic surfactant, said mixing being continued until a homogeneous mixture is produced.

In this process the order of the reacted steps can be varied. Thus, said step (A) and said step (C) can be carried out simultaneously, or the step (A) can precede the step (C).

A presently preferred class of composition of this invention is preferably prepared by the foregoing process and such class comprises compositions containing on a 100 weight percent total concentrate composition basis:

(A) from about 0.2 to 2.0 weight percent of purified growth promoter,
(B) from about 0.2 to 2.0 weight percent of nonionic emulsifier,
(C) from about 0.04 to 0.4 weight percent of preservative,
(D) from about 99.5 to 95.6 weight percent of water.

Preferably such nonionic emulsifier is selected from the group consisting of ethoxylated oleyl alcohol and ethoxylated lauryl alcohol. Preferably, such preservative is selected from the group consisting of 4-hydroxybenzoic acid methyl ester and 4-hydroxybenzoic acid propyl ester.

A preferably preferred sprayable composition for application to plants to achieve plant growth promotion comprises in combination:

(A) a foregoing concentrate composition, and
(B) additional water admixed herewith.

The interrelationship between (A) and (B) in such a composition is preferably such that the concentration of such plant growth promoter in any given such composition ranges from about 0.05 to 5,000 milligrams (mg) per liter (l). More preferably, the concentration of plant growth promoter present therein ranges from about 0.1 to 10 mg per l.

The present invention further provides a method for achieving plant growth promotion which comprises applying to exterior surface portions of a plant a phytologically effective amount of a plant growth promoter of the present invention.

The plant treated can be either a broad leaf plant or a grass plant. The treatment can be accomplished either preemergently, or post-emergently. A combination of such treatments can be used.

In general, usage of the plant growth promoter of this invention is now believed (based upon available observations) to promote (increase);

(a) plant size (particularly height) and leaf development, and
(b) plant fruit yield (individual length and total yield per plant).

However, species variations in results are possible.

The plant growth promoter is suitable for application to a plurality of plants being cultured in a field for crop purposes. Such an application can be carried out preemergently and/or post-emergently (preferably the latter). Such an application is carried out at field dose ranging from about 0.5 to 5.0 grams per hectare with successive field doses being applied timed at intervals ranging from about 15 to 30 days each with each such application being commenced when the plants being treated are approximately 25 days old and being terminated when said plants are within not less than about 25 days of crop harvesting. Examples of crops for which such method is suitable include sorghum, such as Jowar, Sorghum bicolor variety CSH-5.

In such field applications, the plant growth promoter preferably is purified before said applying, preferably using the technique herein described. In such field applications, as in other post-emergent application situations, applying is preferably accomplished by spraying an aqueous emulsion of such plant growth promoter, particularly directly upon leafy surfaces of the plant(s) being treated. The concentration of plant growth promoter in such an aqueous emulsion at the time of said spraying preferably ranges from about 0.05 to 5,000 milligrams per liter, and more preferably from about 0.1 to 10 milligrams per liter. It is presently preferred to use an aqueous emulsion of the type herein described.

A phytologically effective dose rate can vary considerably from one plant species to another and is also dependent upon conditions existing at the time of application so that it is not possible to specify a single dose rate suitable for all plants under all conditions of use possible for a plant growth promoter of this invention. For most crop application (field use) situations, it now appears that an effective dose falls in the range from about 0.5 to 5.0 grams per hectare. Successive doses are applied at intervals ranging from about 15 to 30 days each with such applying preferably first commenced when the plants being treated are approximately 25 days old. Treatment is terminated when treated plants are within not less than about 25 days of crop harvesting.

Embodiments

The foregoing examples are merely illustrative of the present invention and are not intended as a limitation upon the scope thereof.

EXAMPLE 1

1 Kg of a final rice bran fatty acid distillation residue having a typical analysis approximately as above stated was saponified with 500 gm of sodium hydroxide (45% by weight solids) and 1 liter of water in a 'Kadai' (vessel with a hand paddle). Completion of saponification was ascertained by the estimation of unsaponified wax by column chromatography. To the resulting mass having free alkalinity of 6% by weight NaOH, 4.5 liters of water was added to form a solution having a total solids content of 14% by weight. To this solution, saturated calcium chloride aqueous solution (0.6 liters) containing 0.4 kg fused calcium chloride was added and the mixture was thoroughly stirred to effect complete precipitation of calcium soap. The mixture (8 kg) was thereafter filtered in a basket centrifuge to a cake which was transferred into a tray and dried in an air oven at 135° C. for 3 hours. The dried cake weighing 1.2 kg and having a moisture content below 1% was scrapped off from the tray, charged into a cloth bag and extracted in a continuous extractor of the soxhlet type with hot acetone (4 liters) for a period of 12 hours. The temperature of extraction ranged from 40° C. to 50° C. over this period. The extracted solution was concentrated by distilling off the acetone in a distiller to give a 20% solution (w/v). The concentrated solution was left in the distiller overnight to crystallize the fatty alcohols therein and was thereafter filtered in a funnel with filter paper to a cake which was washed with acetone at room temperature. The acetone washed and dried cake weighed 12% by weight of the starting final rice bran fatty acid distillation residue and contained 20% by weight of triacontanol, with the remaining percentages thereof being sterols, other fatty alcohols, wax, and some impurities.

EXAMPLE 2

The process of Example 1 was repeated using a first rice bran fatty acid distillation residue having a typical analysis approximately as above stated instead of the final rice bran fatty acid distillation residue. The acetone washed cake weighed 7.5% of the first rice bran fatty acid distillation residue and contained 20% by weight of triacontanol, with the remaining percentages being mainly sterols, other fatty alcohols, wax, and some impurities.

EXAMPLE 3

0.5 gm of the plant growth promoter (acetone washed solid mass mixed 50:50 from examples 1 and 2 above), 0.5 gm of ethoxylated lauryl alcohol and 0.1 gm methyl paraben were mixed together in 98.9 milliliters of water in a vessel at 85° C. using an ultron stirrer to form an aqueous stable emulsion concentrate.

The aqueous stable emulsion concentrate was diluted with 1,000 parts by weight of water in a vessel equipped with a hand-stirrer and sprayed on Jowar, Sorghum bicolor variety CSH-5, in Satara District of Maharashtra, India. Spraying was done in one half of a twenty acres large block. The other half of said twenty acres large block was not sprayed with the emulsion. The first spraying was done four weeks after transplantation and the subsequent sprayings were done after every three weeks until the flowering stage. The yields of treated and untreated Jowar, Sorghum bicolor variety CSH-5 are given in the following table:

TABLE

| Sr. No. | Parameters Observed | Treatments Sprayed | Treatments Unsprayed | F-Values Observed | F-Values Required | C.V. % | Remarks |
|---|---|---|---|---|---|---|---|
| 1. | Total plant height | 120.06 cms | 108.4 cms | 5.22 | 4.41 | 17.83 | Significant |
| 2. | Earhead length | 27.4 cms | 23.5 cms | 9.59 | 4.41 | 19.32 | Significant |
| 3. | Stem thickness | 1.99 cms | 1.86 cms | 3.06 | 4.41 | 11.90 | Not Significant |
| 4. | Grain yield | 4191.25 Kg/ha | 3709.00 Kg/ha | 5.277 | 4.41 | 11.06 | Significant |
| 5. | Podder yield | 7126.50 Kg/ha | 5610.50 Kg/ha | 928.94 | 4.41 | 23.87 | Significant |

It is quite clear from the Table that the aqueous stable emulsion promoted the growth of Jowar, Sorghum bicolar variety CSH-5 significantly.

Having now fully described the invention, it will be apparent to one of ordinary skill in the art that many changes and modifications can be made thereto without departing from the spirit or scope of the invention as set forth herein.

We claim:

1. A process for the preparation of a plant growth promoter comprising the sequential steps of:
    (A) saponifying under aqueous liquid phase conditions with alkali metal hydroxide a starting material consisting essentially of a residue,
        (1) said residue having been derived from the distillation of crude fatty acids,
        (2) said crude fatty acids having been derived from crude rice bran oil by at least one process selected from the group consisting of
            (a) distillative deacidification, and
            (b) hydrolysis,
        (3) said residue being characterized by comprising on a 100 weight percent total residue basis:
            (a) from about 28 to 44.5 weight percent unsaponifiables,
            (b) from about 6.8 to 7.2 weight percent free fatty acids, and
            (c) from about 48.7 to 64.3 weight percent glycerides,
        (4) said residue being further characterized by having a saponification value ranging from about 88.7 to 130.2,
    thereby to produce a resulting saponified reaction mixture containing alkali metal orgaic salts,
    (B) contacting under aqueous liquid phase conditions alkaline earth metal salt with said resulting saponified reaction mixture, thereby to convert said alkali metal organic salts into alkaline earth metal salts, and
    (C) separating the solids produced from said contacting from the resulting associated liquid phase.

2. The process of claim 1 wherein said saponifying is carried out by employing an initial weight ratio of said alkali metal hydroxide to said residue in the range from about 1:6 to 1:3 .

3. The process of claim 1 wherein said saponifying is carried out at a temperature ranging from about 80° to 100° C. for a time inversely extending from about 5 to 10 hours.

4. The process of claim 1 wherein the liquid comprising said liquid phase is water.

5. The process of claim 1 wherein the liquid comprising said liquid phase is a mixture of water and organic liquid.

6. The process of claim 1 wherein the liquid comprising said liquid phase itself comprises from about 100 to 200 weight percent of the total said resulting saponified reaction mixture.

7. The process of claim 1 wherein said contacting is carried out by employing an initial weight ratio of said alkaline earth metal salt to total estimated said alkali metal organic salts in said resulting saponified reaction mixture in the range from about 1:2 to 1:1.

8. The process of claim 1 wherein said contacting is carried out at a temperature ranging from about 25° to 50° C. for a time inversely extending from about 30 to 60 minutes.

9. The process of claim 1 wherein said alkali metal hydroxide is selected from the group consisting of sodium hydroxide and potassium hydroxide.

10. The process of claim 1 wherein said alkali earth metal salt is selected from the group consisting of calcium chloride, barium chloride, and strontium chloride.

11. The process of claim 1 wherein said separated solids are dried.

12. A process for purifying a solid plant growth promoter of the type produced by practicing the process steps of claim 11, said purification process comprising the steps of:
  (A) subjecting said solid plant growth promoter to extraction with an organic solvent and separating the resulting solution from residual solids, said subjecting being carried out at a temperature ranging from about 40° to 55° C.,
  (B) vaporizing by distillation said organic solvent from said resulting solution at least until a solid precipitate appears in the residual resulting solution,
  (C) separating said solid precipitate from said residual solution, and
  (D) washing said so separated solids with an organic solvent.

13. The plant growth promoter produced by the process of claim 12, said plant growth promoter being characterized by containing on a 100 weight percent total weight basis:
  (A) from about 15 to 25 weight percent of triacontanol, and
  (B) the balance up to 100 weight percent thereof being a mixture which is comprised of sterols, other fatty alcohols, wax, and impurities.

14. A storage stable concentrate composition for water dilution and subsequent plant treatment comprising on a 100 weight percent total composition basis:
  (A) from about 0.2 to 2.0 weight percent of a plant growth promoter of claim 12,
  (B) from about 0.2 to 2.0 weight percent of a nonionic emulsifier selected from the group consisting of ethoxylated oleyl alcohols and ethoxylated lauryl alcohols,
  (C) from about 0.4 to 0.4 weight percent of a preservative selected from the group consisting of 4-hydroxybenzoic acid methyl ester, and 4-hydroxybenzoic acid propyl ester, and
  (D) from about 99.5 to 95.6 weight percent of water.

15. A process for preparing a concentrate composition comprising the steps of
  (A) dissolving from about 0.2 to 2.0 parts by weight of nonionic surfactant in from about 99.5 to 95.6 parts by weight of water,
  (B) dissolving from about 0.04 to 0.4 parts by weight of preservative in said water, and
  (C) mixing from about 0.2 to 2.0 parts by weight of a plant growth promoter of claim 12 with said water while maintaining a temperature in the range from about 60° to 95° C., said mixing being carried out in the presence of said nonionic surfactant, said mixing being continued until a homogeneous mixture is produced.

16. The process of claim 15 wherein said step (A) and said step (C) are carried out simultaneously.

17. The plant growth promoter produced by the process of claim 1.

18. The process of claim 1 wherein such so separated solids are purified.

19. A process for purifying a solid plant growth promoter of the type produced by utilizing process steps as described in claim 1, said purifying process comprising the steps of:
  (A) subjecting said solid plant growth promoter to extraction with an organic solvent and separating the resulting solution from residual solids,
  (B) vaporizing said organic solvent from said resulting solution at least until a solid precipitate appears in the residual resulting solution,
  (C) separating said solid precipitate from said residual solution, and
  (D) washing said so separated solids with an organic solvent.

20. The process of claim 19 wherein said subjecting is carried out with said organic solvent being selected from the group consisting of acetone and isopropanol.

21. The process of claim 19 wherein said subjecting is carried out at a temperature ranging from about 40° to 55° C.

22. The process of claim 19 wherein said vaporizing is carried out by distillation.

23. The process of claim 19 wherein said washing is carried out with said organic solvent being selected from the group consisting of acetone and isopropanol.

24. The process of claim 19 wherein after said washing the resulting solids are dried.

25. The plant growth promoter produced by the process of claim 19, said plant growth promoter being characterized by containing on a 100 weight percent total weight basis:
  (A) from about 15 to 25 weight percent of triacontanol, and
  (B) the balance upto 100 percent thereof being a mixture which is comprised of sterols, other fatty alcohols, wax, and impurities.

26. A method for achieving plant growth promotion comprising applying to exterior surface portions of a plant a phytologically effective amount of a plant growth promoter of the type produced by utilizing a process of claim 1.

27. The method of claim 26 wherein said applying is accomplished by spraying an aqueous emulsion of said plant growth promoter.

28. The method of claim 26 wherein said plant is a broad leaf plant.

29. A method for achieving plant growth promotion of plants being cultured in a field for crop purposes comprising applying to said plants an aqueous emulsion of claim 28 at a phytologically effective dose rate.

30. The method of claim 29 wherein said dose rate ranges from about 0.5 to 5.0 grams per hectare with successive doses being applied at intervals ranging from about 15 to 30 days each with said applying being commenced when said plants are approximately 25 days old and being terminated when said plants are within not less than about 25 days of crop harvesting.

31. The method of claim 30 wherein said crop is sorghum.

32. The method of claim 26 wherein said plant is a grass plant.

33. The method of claim 26 wherein said plant growth promoter is so applied pre-emergently.

34. The method of claim 26 wherein said plant growth promoter is so applied post-emergently.

35. The method of claim 26 wherein said plant growth promoter is so applied to a plurality of said plants being cultured in a field for crop purposes.

36. The method of claim 35 wherein said applying is carried out pre-emergently and post-emergently.

37. The method of claim 35 wherein said applying is carried out at a dose rate ranging from about 0.5 to 5.0 grams per hectare with successive doses being applied at intervals ranging from about 15 to 30 days each with said applying being commenced when said plants are approximately 25 days old and being terminated when said plants are within not less than about 25 days of crop harvesting.

38. The method of claim 35 wherein said plants comprise sorghum.

39. The method of claim 38 wherein said plants comprise Jowar, Sorghum bicolor variety CSH-5.

40. The method of claim 26 wherein said plant growth promoter is purified before said applying.

41. The method of claim 40 wherein said applying is accomplished by spraying an aqueous emulsion of said plant growth promoter.

42. The method of claim 41 wherein the concentration of said plant growth promoter in said aqueous emulsion at the time of said spraying ranges from about 0.05 to 5,000 milligrams per liter.

43. The method of claim 42 wherein said concentration ranges from about 0.1 to 10 milligrams per liter.

44. A process for the preparation of a plant growth promoter comprising the sequential steps of:
(A) saponifying under aqueous liquid phase conditions with an alkali metal hydroxide selected from the group consisting of sodium hydroxide and potassium hydroxide a starting material consisting essentially of a residue,
  (1) said residue having been derived from the distillation of crude fatty acids,
  (2) said crude fatty acids having been derived from crude rice bran oil by at least one process selected from the group consisting of
    (a) distillative deacidification and
    (b) hydrolysis,
  (3) said residue being characterized by comprising on a 100 weight percent total residue basis:
    (a) from about 28 to 544.5 weight percent
    (b) from about 6.8 to 7.2 weight percent free fatty acids, and
    (c) from about 48.7 to 64.3 weight percent glycerides,
  (4) said residue being further characterized by having a saponification value ranging from about 88.7 to 130.2,
thereby to produce a resulting saponified reaction mixture containing alkali metal organic salts, said saponifying being carried out while
  (1) employing an initial weight ratio of said alkali metal hydroxide to said residue in the range from about 1:6 to 1:3,
  (2) maintaining a temperature ranging from about 80° to 100° C. for a time inversely extending from about 5 to 10 hours, and
  (3) utilizing a liquid phase which itself comprises from about 100 to 200 weight percent of the total weight of said resulting saponified reaction mixture,
(B) contacting under aqueous liquid phase conditions on alkaline earth metal salt selected from the group consisting of calcium chloride, barium chloride, and strontium chloride with said resulting saponified reaction mixture, thereby to convert said alkali metal organic salts into alkaline earth metal salts, said contacting being carried out while,
  (1) employing an initial weight ratio of said alkaline earth metal salt to total estimated said alkali metal organic salts in said resulting saponified reaction mixture in the range from about 1:2 to 1:1,
  (2) maintaining a temperature ranging from about 25° to 50° C. for a time inversely extending from about 30 to 60 minutes,
(C) separating the solids produced from said contacting from the resulting associated liquid phase, and
(D) drying the so separated solids.

45. The process of claim 44 wherein said residue is selected from the group consisting of first rice bran fatty acid distillation residues and final rice bran fatty acid distillation residues.

46. The process of claim 44 wherein such so separated solids are purified.

47. The plant growth promoter produced by the process of claim 44.

48. A storage-stable emulsified concentrate composition for dilution with water and subsequent treatment of plants, and which does not adversely affect absorption of minerals comprising on a 100 weight percent total concentrate composition basis:
(a) from about 0.2 to 2.0 weight percent of a growth promoter produced by the process of claim 47,
(b) from about 0.2 to 2.0 weight percent of nonionic emulsifier,
(c) from about 0.04 to 0.4 weight percent of preservative, and
(d) from about 99.5 to 95.6 weight percent of water.

49. The composition of claim 48 wherein said preservative is selected from the group consisting of 4-hydroxybenzoic acid methyl ester, and 4-hydroxybenzoic acid propyl ester.

50. The process of claim 49 wherein said step (A) precedes said step (C).

51. The composition of claim 48 wherein said nonionic emulsifier is selected from the group consisting of ethoxylated oleyl alcohol and ethoxylated lauryl alcohol.

52. A sprayable composition for application to plants to achieve plant growth promotion comprising, in combination,
(A) the concentrate composition of claim 48, and
(B) additional water,
the interrelationship between (A) and (B) being such that the concentration of said plant growth promoter in any given said sprayable composition ranges from about 0.05 to 5,000 milligrams per liter.

53. A process for the preparation of a plant growth promoter from rice bran fatty acid distillation residue, said process comprising saponifying said residue with an aqueous alkali metal hydroxide, treating the resulting reaction mixture with an alkaline earth metal salt, filtering the reaction mixture, drying the solids obtained, extracting the dried solids with an organic solvent, concentrating the extract solution, filtering the concentrated extract solution, and washing the recovered solids with an organic solvent to obtain the desired plant growth promoters.

54. A process for the preparation of a plant growth promoter comprising the sequential steps of:
(A) saponifying under aqueous liquid phase conditions with alkali metal hydroxide a starting material consisting essentially of a residue,
  (1) said residue having been derived from the distillation of crude fatty acids,
  (2) said crude fatty acids having been derived from crude rice bran oil by at least one process selected from the group consisting of
    (a) distillative deacidification and
    (b) hydrolysis,
  (3) said residue being characterized by comprising on a 100 weight percent total residue basis;

(a) from about 28 to 44.5 weight percent unsaponifiables,
(b) from about 6.8 to 7.2 weight percent free fatty acids,
(c) from about 48.7 to 64.3 weight percent glycerides,
(4) said residue being further characterized by having a saponification value ranging from about 88.7 to 130.2, thereby to produce a resulting saponified reaction mixture containing alkali metal organic salts, (B) contacting under aqueous liquid phase conditions alkaline earth metal salt with said resulting saponified reaction mixture, thereby to convert said alkali metal organic salts into alkaline earth metal salts, (C) separating the solids produced from said contacting from the resulting associated liquid phase, (D) subjecting said separated solids to extraction with an organic solvent and then separating the resulting extract solution from residual solids, (E) vaporizing said organic solvent from said resulting solution at least until a solid precipitate appears in such residual resulting solution, (F) separating said solid precipitate from said residual solution, and (G) washing said so separated solid precipitate with an organic solvent.

55. The process of claim 54 wherein said separated solids are dried in air at about 130° to 140° C. for about three hours.

56. The process of claim 54 wherein said subjecting is carried out with said organic solvent being at a temperature in the range from about 40° to 55° C.

* * * * *